US 6,666,127 B2

(12) United States Patent
Peles

(10) Patent No.: US 6,666,127 B2
(45) Date of Patent: Dec. 23, 2003

(54) ARTIFICIAL MUSCLE

(75) Inventor: Zalman Peles, Kfar Korazim (IL)

(73) Assignee: Muscle Tech Ltd., Katzrin (IL)

( * ) Notice: Subject to any disclaimer, the term of this patent is extended or adjusted under 35 U.S.C. 154(b) by 0 days.

(21) Appl. No.: 10/137,387

(22) Filed: May 3, 2002

(65) Prior Publication Data

US 2003/0205045 A1 Nov. 6, 2003

(51) Int. Cl.[7] .............................................. F01B 19/00
(52) U.S. Cl. .................... 92/50; 92/75; 92/90; 623/26
(58) Field of Search ................... 60/473, 476; 92/50, 92/69 R, 75, 90, 89, 92; 623/14, 13, 26

(56) References Cited

U.S. PATENT DOCUMENTS

| 4,784,042 A | 11/1988 | Paynter |
| 4,958,705 A | 9/1990 | Horvath |
| 5,031,510 A | 7/1991 | Krauter |
| 5,067,390 A | * 11/1991 | Negishi ........................ 92/92 |
| 5,322,468 A | * 6/1994 | Smrt ........................ 446/199 |
| 5,379,664 A | 1/1995 | Kershaw et al. |
| 5,800,561 A | 9/1998 | Rodriguez |
| 6,067,892 A | 5/2000 | Erickson |
| 6,168,634 B1 | 1/2001 | Schmitz |
| 6,178,872 B1 | 1/2001 | Schulz |

OTHER PUBLICATIONS

"Irrigated Muscle"—MIT http://www.ai.mit.edu/projects/muscle/papers/memo1330/memo1330.html.
"McKibben Muscle" http://brl.ee.washington.edu/BRL/devices/mckibben/index.html.

* cited by examiner

Primary Examiner—Edward K. Look
Assistant Examiner—Thomas E. Lazo
(74) Attorney, Agent, or Firm—Mark M. Friedman

(57) ABSTRACT

A hydraulically actuated artificial muscle for use with orthetic devices, prosthetic devices or as an actuator for other applications in medical or robotic devices. Working fluid is pumped between two expandable fluid-containing cells, which are complimentary active elements of the artificial muscle. This eliminates the need for a storage reservoir, thereby providing a self-contained, force efficient device. Each of the preferred embodiments described has one or more expandable fluid-containing cell defined by at least one flexible wall. The flexible walls are configured so as to have elastic properties that are limited to predefined directions of expansion and contraction.

22 Claims, 8 Drawing Sheets

ARTIFICIAL MUSCLE

FIELD AND BACKGROUND OF THE INVENTION

The present invention relates to artificial muscles and, in particular, it concerns hydraulic actuated artificial muscles for use with orthetic devices, prosthetic devices or as an actuator for other applications in medical and robotic devices.

The principles of hydraulics have been used in the development of innumerable devices where pushing or pulling forces were need. These were generally based on rigid hydraulic cylinders and pistons. Recent years have seen the development of pushing and pulling devices that are intended to imitate muscle tissue both in the manner in which they operate and in texture. As a result, there is now a class of devices generally referred to as "muscles."

Some of the muscle devices are based on polymers that can be made to contract as a result of chemical changes or an electric current, such as the "Irrigated Muscle" being researched at M.I.T. (www.ai.mit.edu/projects/muscle/papers/memo1330/memo1330.html). Research is also under way at the University of New Mexico on a combination of polymer and metal strips which are made to contract by the use of electric current (www.unm. edu/%7Eamri/). Devices based on these types of technology may act in a way similar to natural muscle and may be suited to robotic applications. They may, however, be inappropriate for applications entailing close contact with a human body, such as orthetics.

Another group of artificial muscles are based on the principles of pneumatics, such as the "McKibben Muscle" technology of the University of Washington (http://brl.ee.washington.edu/BRL/devices/mckibben/index.html). Closely related to the pneumatic muscles are those muscle devices based on hydraulics. The obvious similarity is that movement is due to the expansion of a device component due to fluid pressure, either air pressure or liquid pressure. In fact, many of the artificial muscles in these groups may be suitable for pneumatic or hydraulic applications. These devices, also, suffer either collectively or individually from a number of drawbacks. The devices of U.S. Pat. No. 4,784,042 to Payuter, U.S. Pat. No. 5,245,885, to Robertson, 6,067,892 to Erickson and U.S. Pat. No. 6,168,643 B1 to Schmitz are representative of devices that suffer from the need to be connected to external support devices such as air compressors, hydraulic pumps and fluid reservoirs. These external support devices are usually heavy cumbersome pieces of equipment, ill suited for a target goal of bringing mobility to patients with limited or no use of one or more of their limbs. Further, these devices are able to apply force in only one direction.

The hydraulic device of U.S. Pat. No. 4,958,705 to Horvath eliminates the need for an external fluid reservoir. The pneumatic device of U.S. Pat. No. 5,800,561 to Rodriguez eliminates the need for a compressor by utilizing a small canister of compressed air. The amount of usage is reliant upon the size and pressure limitations of the canister. Both these devices, however, offer no inherent cushioning for any soft tissue they may contact.

There is therefore a need for a self-contained artificial muscle that is able to exert enough force to actuate an orthetic device or prosthetic device. That is, an artificial muscle that does not need to be connected to external support devices, such as air compressors and fluid reservoirs. It would be desirable if the artificial muscle can be directed to apply force in more than one direction; that is, either a pushing force or a pulling force, as needed. It would be further desirable if the artificial muscles could provide an amount of cushion or other protection for any soft tissue it may contact during use without the use of additional coverings.

SUMMARY OF THE INVENTION

The present invention is a hydraulic actuated artificial muscle.

According to the teachings of the present invention there is provided, a method for causing relative movement between at least two connecting elements, the at least two connecting elements being for attaching a hydraulic actuator to an application device, the method comprising: transferring fluid between at least one first expandable fluid-containing cell and at least one second expandable fluid-containing cell such that the transferring of fluid out of one of the first expandable fluid-containing cell and the second expandable fluid-containing cell and into an other of the first expandable fluid-containing cell and the second expandable fluid-containing cell thereby causing substantially simultaneous contracting of the one and expanding of the other of the first expandable fluid-containing cell and the second expandable fluid-containing cell, the transferring being performed using a pump system in fluid communication with the first expandable fluid-containing cell and the second expandable fluid-containing cell thereby forming a closed fluid system; wherein the at least one first expandable fluid-containing cell is at least partially defined by a first displaceable containment-wall, the first expandable fluid-containing cell being mechanically linked to at least a first of the connecting elements, the at least one second expandable fluid-containing cell is at least partially defined by a second displaceable containment-wall, the second expandable fluid-containing cell being mechanically linked to at least a second of the connecting elements, and at least one of the first displaceable containment-wall and second displaceable containment-wall is a flexible wall and the expanding of each the expandable fluid-containing cell generates relative movement between at least two of the connecting elements.

According to a further teaching of the present invention, the transferring is of an incompressible fluid.

According to a further teaching of the present invention, the transferring is performed between the at least one first expandable fluid-containing cell and the at least one second expandable fluid-containing cell configured such that one of the first displaceable containment-wall and second displaceable containment-wall defines at least portions of both the first expandable fluid-containing cell and the second expandable fluid-containing cell.

According to a further teaching of the present invention, the transferring is performed between the at least one first expandable fluid-containing cell and the at least one second expandable fluid-containing cell configured such that the first expandable fluid-containing cell substantially circumscribes the second expandable fluid-containing cell.

According to a further teaching of the present invention, the transferring is performed such that the expanding of the first expandable fluid-containing cell and the expanding of the second expandable fluid-containing cell are such that as fluid is pumped out of the first expandable fluid-containing cell and into the second expandable fluid-containing cell, the second expandable fluid-containing cell expands, thus causing the hydraulic actuator to expand longitudinally while contracting latitudinally thereby causing at least two of the connection elements to move substantially away from each other, conversely as fluid is pumped out of the second expandable fluid-containing cell and into the at least a first expandable fluid-containing cell, the first expandable fluid-containing cell expands, thus causing the hydraulic actuator to contract longitudinally while expanding latitudinally thereby causing at least two of the connection elements to move substantially toward each other.

According to a further teaching of the present invention, the transferring is performed between the at least one first expandable fluid-containing cell and the at least one second expandable fluid-containing cell configured such that both the first displaceable containment-wall and the second displaceable containment-wall are implemented as flexible walls.

According to a further teaching of the present invention, the transferring is performed between the at least one first expandable fluid-containing cell and the at least one second expandable fluid-containing cell configured such that the second displaceable containment-wall is implemented as a cylindrical wall of a piston element of a cylinder and piston assembly, the piston being displaceable within the cylinder.

According to a further teaching of the present invention, the transferring is performed between the at least one first expandable fluid-containing cell and the at least one second expandable fluid-containing cell configured such that the first expandable fluid-containing cell is deployed on a first side of a central base, the central base including at least a first of the connecting element, and second expandable fluid-containing cell is deployed on a second side of the central base, at least a second of the connecting elements is attached to the first expandable fluid-containing cell, at least a third of the connecting elements is attached to the at least one second expandable fluid-containing cell, the expanding of the first expandable fluid-containing cell and the expanding of the second expandable fluid-containing cell are such that as the fluid is pumped out of the first expandable fluid-containing cell and into the second expandable fluid-containing cell, the second expandable fluid-containing cell expands, thereby causing a first at least two of the connection elements to move substantially away from each other, conversely as fluid is pumped out of the second expandable fluid-containing cell and into the first expandable fluid-containing cell, the first expandable fluid-containing cell expands, thereby causing a second at least two of the connection elements to move substantially away from each other.

According to a further teaching of the present invention, the transferring is performed between the at least one first expandable fluid-containing cell and the at least one second expandable fluid-containing cell configured such that both the at least a first displaceable containment-wall and the at least a second displaceable containment-wall are implemented as the flexible walls.

According to a further teaching of the present invention, the transferring is performed between the at least one first expandable fluid-containing cell and the at least one second expandable fluid-containing cell configured such that the first side and the second side are substantially opposite sides of the central base.

According to a further teaching of the present invention there is also provided, the transferring being performed so as to articulate an orthetic device.

According to a further teaching of the present invention, the transferring being performed so as to articulate a prosthetic device.

There is also provided according to the teachings of the present invention, a hydraulic actuator comprising: at least two connecting elements for attaching the hydraulic actuator to an application device; at least one first expandable fluid-containing cell at least partially defined by a first displaceable containment-wall, the first expandable fluid-containing cell being mechanically linked to at least a first of the connecting elements; at least one second expandable fluid-containing cell at least partially defined by a second displaceable containment-wall, the second expandable fluid-containing cell being mechanically linked to at least a second of the connecting elements; and a pump system in fluid communication with the first expandable fluid-containing cell and the second expandable fluid-containing cell thereby forming a closed fluid system, the pump system configured to transfer fluid out of one of the first expandable fluid-containing cell and the second expandable fluid-containing cell and into an other of the first expandable fluid-containing cell and the second expandable fluid-containing cell, thereby causing substantially simultaneous contraction of the one and expansion of the other of the first expandable fluid-containing cell and the second expandable fluid-containing cell; wherein at least one of the first displaceable containment-wall and second displaceable containment-wall is a flexible wall and the expansion of each the expandable fluid-containing cell generates relative movement between at least two of the connecting elements.

According to a further teaching of the present invention, the fluid is an incompressible fluid.

According to a further teaching of the present invention, one of the first displaceable containment-wall and second displaceable containment-wall defines at least portions of both the first expandable fluid-containing cell and the second expandable fluid-containing cell.

According to a further teaching of the present invention, the first expandable fluid-containing cell substantially circumscribes the second expandable fluid-containing cell.

According to a further teaching of the present invention, the expansion of the first expandable fluid-containing cell and the expansion of the second expandable fluid-containing cell are configured such that as fluid is pumped out of the first expandable fluid-containing cell and into the second expandable fluid-containing cell, the second expandable fluid-containing cell expands, thus causing the hydraulic actuator to expand longitudinally while contracting latitudinally thereby causing at least two of the connection elements to move substantially away from each other, conversely as fluid is pumped out of the second expandable fluid-containing cell and into the at least a first expandable fluid-containing cell, the first expandable fluid-containing cell expands, thus causing the hydraulic actuator to contract longitudinally while expanding latitudinally thereby causing at least two of the connection elements to move substantially toward each other.

According to a further teaching of the present invention, both the first displaceable containment-wall and the second displaceable containment-wall are implemented as flexible walls.

According to a further teaching of the present invention, the second displaceable containment-wall is implemented as a cylindrical wall of a piston element of a cylinder and piston assembly, the piston being displaceable within the cylinder.

According to a further teaching of the present invention, the at least two connecting elements are implemented as at least three connecting elements, at least a portion of a first the connecting element being configured as a central base, at least a second the connecting element being attached to the first expandable fluid-containing cell deployed on a first side of the central base and at least a third the connecting elements being attached to the second expandable fluid-containing cell deployed on a second side of the central base, the expansion of the first expandable fluid-containing cell and the expansion of the second expandable fluid-containing cell are such that as fluid is pumped out of the first expandable fluid-containing cell and into the second expandable fluid-containing cell, the second expandable fluid-containing cell expands, thereby causing a first at least two of the connection elements to move substantially away from each other, conversely as fluid is pumped out of the second expandable fluid-containing cell and into the first expandable fluid-containing cell, the first expandable fluid-containing cell expands, thereby causing a second at least two of the connection elements to move substantially away from each other.

According to a further teaching of the present invention, both the at least a first displaceable containment-wall and the at least a second displaceable containment-wall are implemented as the flexible walls.

The hydraulic actuator of claim 20, wherein the first side and the second side are substantially opposite sides of the central base.

According to a further teaching of the present invention, the application device is an orthetic device.

According to a further teaching of the present invention, the application device is a prosthetic device.

BRIEF DESCRIPTION OF THE DRAWINGS

It should be noted that the drawings are schematic and not necessarily to scale, and some discrepancies may exist in relation to illustrated volumetric displacements.

The invention is herein described, by way of example only, with reference to the accompanying drawings, wherein.

DESCRIPTION OF THE PREFERRED EMBODIMENTS

Figure 1:
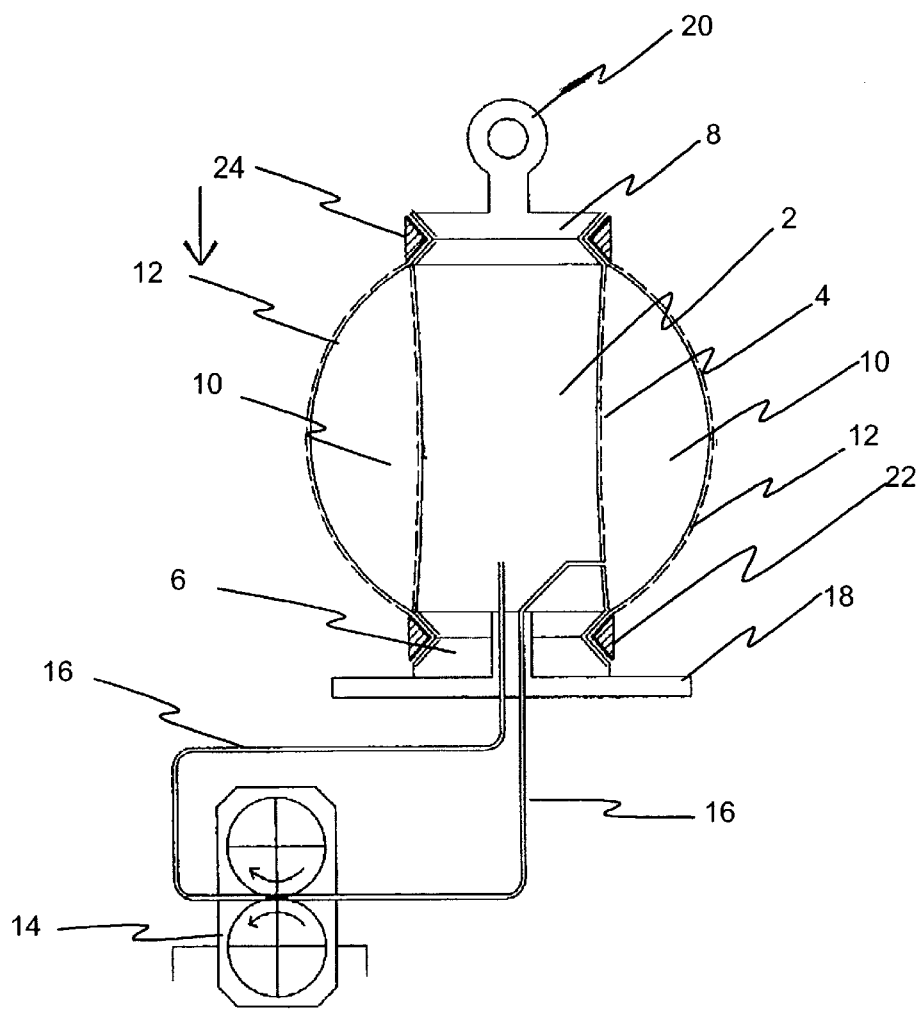
FIG. 1 is a cross-sectional front view of a first preferred embodiment of a hydraulic actuator, constructed and operative according to the teachings of the present invention, with two flexible walls and a first expandable fluid-containing cell circumscribing a second expandable fluid-containing cell, the actuator is shown in its longitudinally shortest disposition.

The present invention is a hydraulic actuated artificial muscle.

The principles and operation of a hydraulic actuated artificial muscle according to the present invention may be better understood with reference to the drawings and the accompanying description.

By way of introduction, one common principle of the embodiments of the present invention is that the hydraulic fluid is pumped between two expandable fluid-containing cells, both of which are active elements of the apparatus. This is in contrast to hydraulic systems that have a non-active fluid reservoir that stores fluid for use in operating one or more active elements.

Another common principle is that of the use of a "flexible wall." Herein used, the term "flexible wall" relates to a wall configured of substantially elastic material having limited direction of stretch. As discussed herein, the present invention utilizes two types of flexible wall material. In both types, the stretch is provided by a material that is fully elastic in all directions, and strong enough to withstand the hydraulic pressures necessary for a particular application, for example, but not limited to, natural rubber, silicon rubber and latex. The stretch limitation is provided by a netting configured with specific directional movement properties. The flexible wall may be configured as two layers, with the netting surrounding the stretchable material, or the netting may be integral to the stretchable material, either fixed to the surface or molded into the stretchable material. A first type of flexible wall will be referred to herein as a unidirectional stretch flexible wall. Unidirectional stretch flexible wall material is configured so as to limit the direction of stretch substantially to a single linear direction of stretch. Unidirectional stretch material may be configured as a cylinder that expands and contracts substantially longitudinally without substantial radial expansion and contraction. This may be accomplished using, by non-limiting, example, braided netting that is known in the art. Another example of material with these properties is a medical elastic bandage, which is extremely stretchable along its length but has substantially not stretch across its width. A second type of flexible wall will be referred to herein as bi-directional stretch flexible wall. Bi-directional stretch flexible wall material is configured to limit the directions of stretch to two substantially perpendicular directions such that as the material is stretched along one axis, it simultaneously contracts along the other, perpendicular, axis. This may be accomplished using substantially conventional netting configured form a non-stretchable material such that the expansion and contraction properties of the netting are a result of the directional changes of the strands of the netting. That is, as the material is pulled in one direction, the strands become more linearly oriented in that direction, thereby allowing expansion in that direction. As a result of this change in linear orientation the material contracts in a direction substantially perpendicular to the direction of expansion. When configured as the flexible wall of an expandable fluid-containing cell, the limited expansion properties of the flexible wall define, for example, the direction of expansion and the shape of the cell. The use of flexible walls softens the contact between the actuator and any bodily tissues the actuator may encounter, thereby adding protection for the tissue.

Further, the term "pump system" is used herein to refer to any device or combination of devices that is capable of transferring fluid between at least two expandable fluid-containing cells. That is, capable of transferring fluid of a first expandable fluid-containing cell to a second expandable fluid-containing cell and then reversing the process to transfer the fluid from the second expandable fluid-containing cell back to the first expandable fluid-containing cell. The list of suitable devices may include, by non-limiting example, bi-directional pumps, a plurality of mono-directional pumps pumping in different directions, and a single mono-directional pump used in conjunction with at least one flow switch. The preferred use herein of the term "fluid" is in reference to incompressible fluids, however, any material with fluid properties suitable for a specific application, including, but not limited to, gases, liquids, and dense or semi-liquids characterized as jells are within the intentions of the present invention.

Referring now to the drawings, the first preferred embodiment of a hydraulic actuator, as shown in FIG. 1, has an inner expandable fluid-containing cell 2 that is defined by a substantially cylindrical inner flexible wall 4, a substantially circular base 6 and a substantially circular top 8. Elements 18, on the base, and 20, on the top, are non-limiting examples of connecting-elements that may be used to attach the actuator to an application device. The inner flexible wall 4 is configured as a unidirectional flexible wall so that the inner expandable fluid-containing cell 2 has limited direction of expansion that is substantially longitudinal. That is, the base 6 and top 8 are pushed away form each other when fluid is pumped into the inner expandable fluid-containing cell 2. The phrases "away from each other," and "toward each other," as used herein, are intended to include, but no be limited to, situations where one element is free to move and the other element is fixed or where both elements are free to move. The outer expandable fluid-containing cell 10 is defined by the inner flexible wall 4 and the outer flexible wall 12 so that the outer expandable fluid-containing cell 10 substantially circumscribes the inner expandable fluid-containing cell 2, so as to encircle the inner flexible wall. It should be noted, that a configuration wherein the outer cell surrounds the inner cell is within the intention of the present invention. The outer flexible wall 12 is configured as a bi-directional flexible wall so that the outer expandable fluid-containing cell 10 contracts longitudinally as it expands substantially latitudinal. Thus, the base 6 and top 3 will be pulled toward each other when fluid is pumped into the outer expandable fluid-containing cell 10. The flexible walls are attached to the base 6 and top 8 by use of retaining rings 22 and 24 respectively. As illustrated here, the pump 14 transfers fluid from the inner expandable fluid-containing cell 2 to the outer expandable fluid-containing cell 10 by way of the fluid transfer tube 16. This transfer of fluid causes the outer expandable fluid-containing cell to expand substantially radially and become substantially spherical in shape, thereby pulling the base 6 and the top 8 toward each other.

Figure 2:
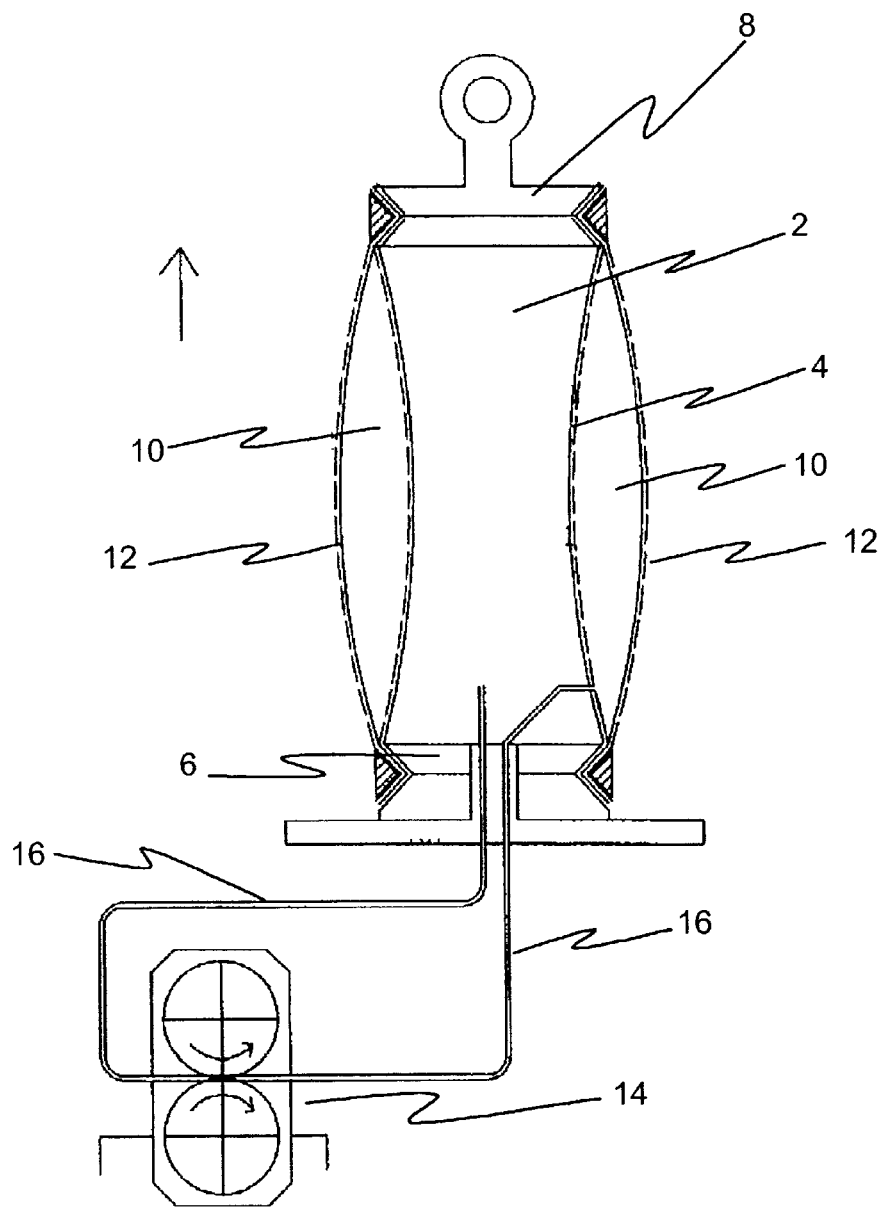
FIG. 2 is a cross-sectional front view of the hydraulic actuator of FIG. 1, shown in its longitudinally longest disposition.

FIG. 2 illustrates the longitudinal expansion of the actuator of FIG. 1. As shown, the transfer of fluid from the outer expandable fluid-containing cell 10 to the inner expandable fluid-containing cell 2 causes a substantially simultaneous displacement of the outer flexible wall 12 and of the inner flexible wall 4. This results in a substantially simultaneous expansion of the inner expandable fluid-containing cell 2 and contraction of the outer expandable fluid-containing cell 10, thereby causing the longitudinal expansion of the actuator. That is, pushing the base 6 and the top 8 substantially away from each other.

So then, FIGS. 1 and 2 respectively illustrate the pull and push strokes of this preferred embodiment of the present invention.

Figure 3:
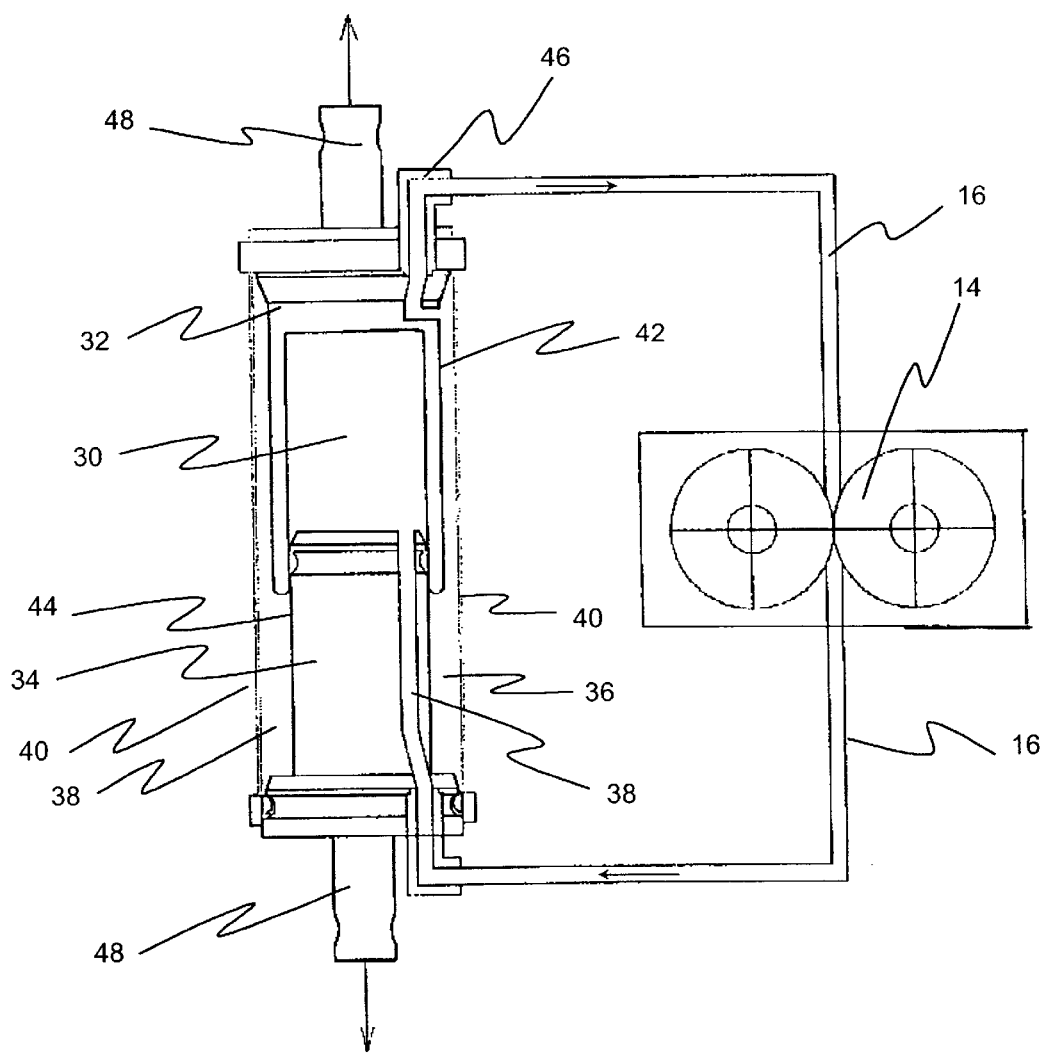
FIG. 3 is a cross-sectional front view of a second preferred embodiment of a hydraulic actuator, constructed and operative according to the teachings of the present invention, with one flexible wall defining a first expandable fluid-containing cell circumscribing a second expandable fluid-containing cell that is configured as a cylinder and piston assembly, the actuator is shown in its longitudinally longest disposition with the cylinder and piston assembly fully extended.

FIG. 3 shows a second preferred embodiment of a hydraulic actuator constructed and operative according to the teachings of the present invention. Here, the inner expandable fluid-containing cell 30 is configured as a cylinder 32 and piston 34 assembly. The outer expandable fluid-containing cell 38 substantially circumscribes the cylinder and piston assembly, and is substantially defined by the outer wall of the cylinder 42, the cylindrical wall of the piston 44, and the flexible wall 40. The piston includes a fluid passageway 38 that connects expandable fluid-containing cell 30 to the fluid transfer tube 16, which in turn passes through the pump 14 and connects to passageway 46 that passes through the cylinder housing and into the outer expandable fluid-containing cell 38. This provides a conduit whereby the pump 14 transfers fluid bi-directionally between the inner expandable fluid-containing cell 30 and the outer expandable fluid-containing cell 36, as needed. As illustrated here, the fluid is pumped from the outer expandable fluid-containing cell into the inner expandable fluid-containing cell, thereby causing the cylinder and piston assembly to expand longitudinally and the outer expandable fluid-containing cell to contract, thereby causing the actuator to expand longitudinally. The non-limiting examples of connecting-elements 48 at either end of the actuator, which may be used to attach the actuator to an application device, move substantially away form each other as the actuator expands.

Figure 4:
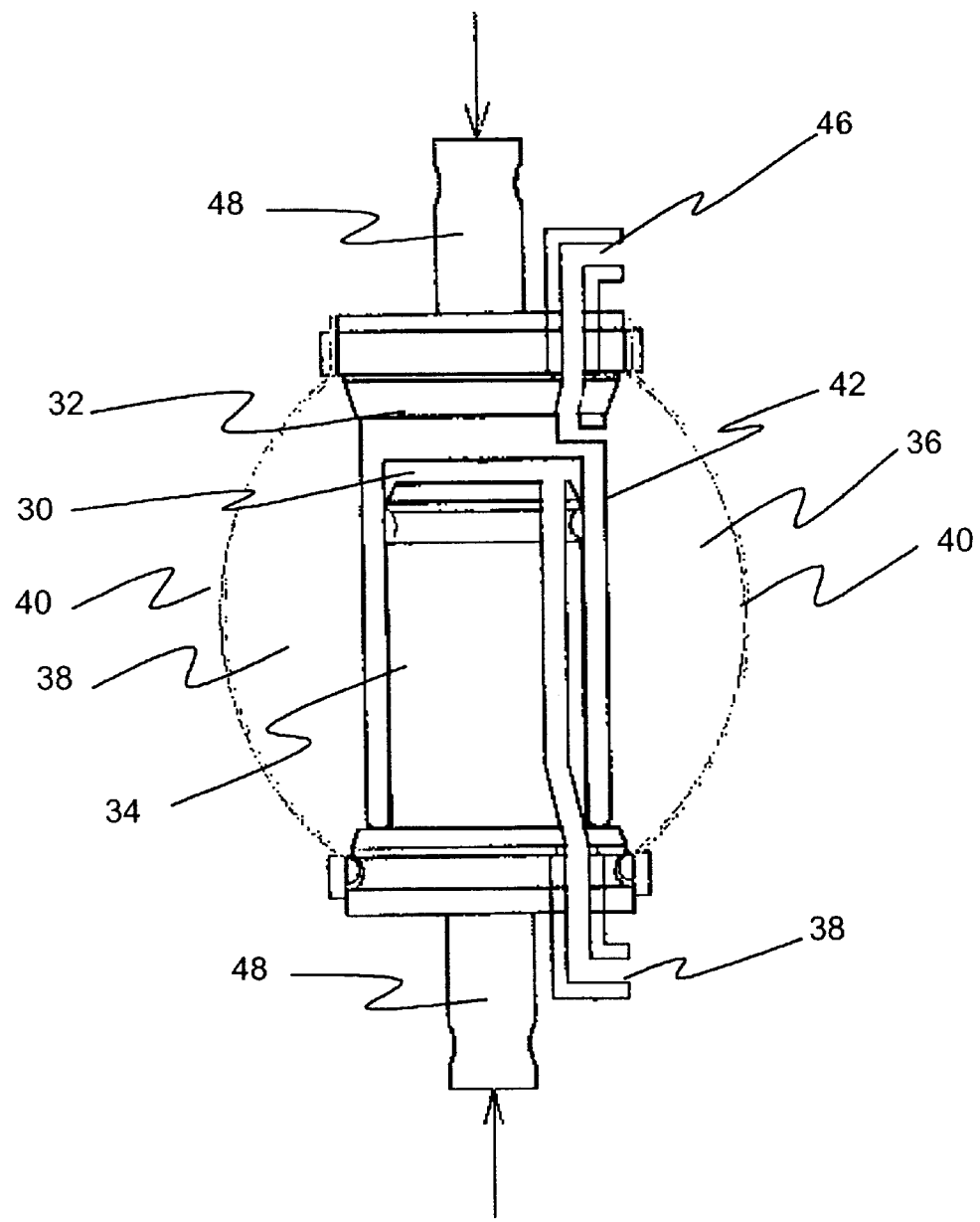
FIG. 4 is a cross-sectional front view of the hydraulic actuator of FIG. 3, shown in its longitudinally shortest disposition.

FIG. 4 shows the second preferred embodiment of FIG. 3 in a contracted state. As illustrated here, the fluid is pumped out of the inner expandable fluid-containing cell 30 and, by way of passageway 38, through the fluid transfer tube, and passageway 46, into the outer expandable fluid-containing cell 36. This transfer of fluid from the inner expandable fluid-containing cell 30 to the outer expandable fluid-containing cell 36 causes the substantially simultaneous expansion of the outer expandable fluid-containing cell and contraction of the cylinder and piston assembly, thereby causing the longitudinal contraction of the actuator, and the connecting-elements to move toward each other.

So then, FIGS. 3 and 4 respectively illustrate the push and pull strokes of this preferred embodiment of the present invention.

Figure 5:
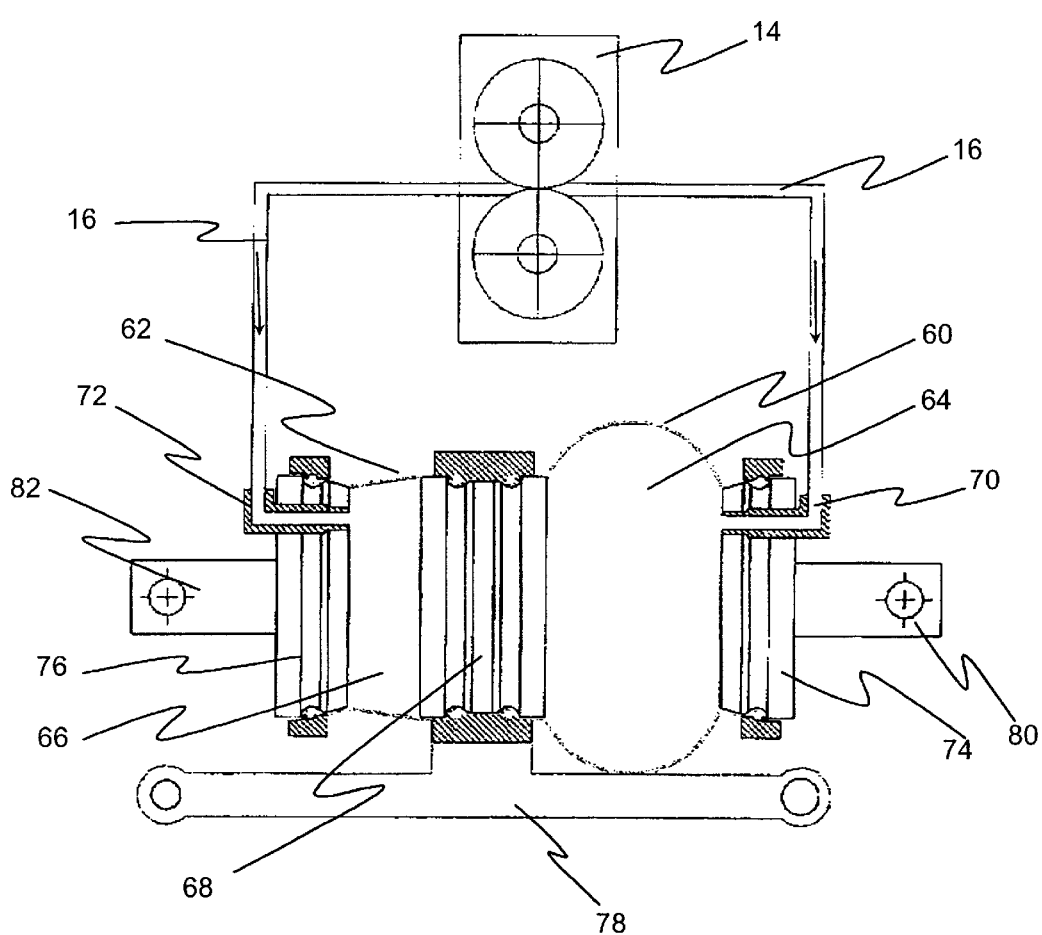
FIG. 5 is a cross-sectional side view of a third preferred embodiment of a hydraulic actuator constructed and operative according to the teachings of the present invention, with two flexible walled expandable fluid-containing cells deployed on opposite sides of a central base, shown with a first side expanded and a second side contracted.

In the third preferred embodiment of the present invention, as illustrated in FIG. 5, each of two flexible walls 60 and 62 are configured as unidirectional flexible walls and are connected to opposite sides of a central base 68 and each of them is further connected end housings 74 and 76 respectively, thereby substantially defining two expandable fluid-containing cells 64 and 66 that are located on opposite sides of a central base 68. The two expandable fluid-containing cells are in fluid communication by way of a conduit including the fluid passageway 70, which is connected to expandable fluid-containing cell 64, the fluid transfer tube 16, the pump 14, and the fluid passageway 72, which is connected to expandable fluid-containing cell 66. The base further includes a base connection-element 78. It should be noted that the base may be configured as the base connection-element. The end housing 74 also includes a connection-element 80, as does the end housing 76 include connection-element 82. As illustrated here, the fluid is pumped into expandable fluid-containing cell 64, the flexible wall 60 is displaced causing expandable fluid-containing cell 64 to expand, and end housing 74, and therefore connection-element 80, to move away from the central base 68 and connection-element 78. Simultaneously, flexible wall 62 also is displaced and expandable fluid-containing cell 66 contracts causing the end housing 76, and therefore connection-element 82, to move toward the central base 68 and connection-element 78.

Figure 6:
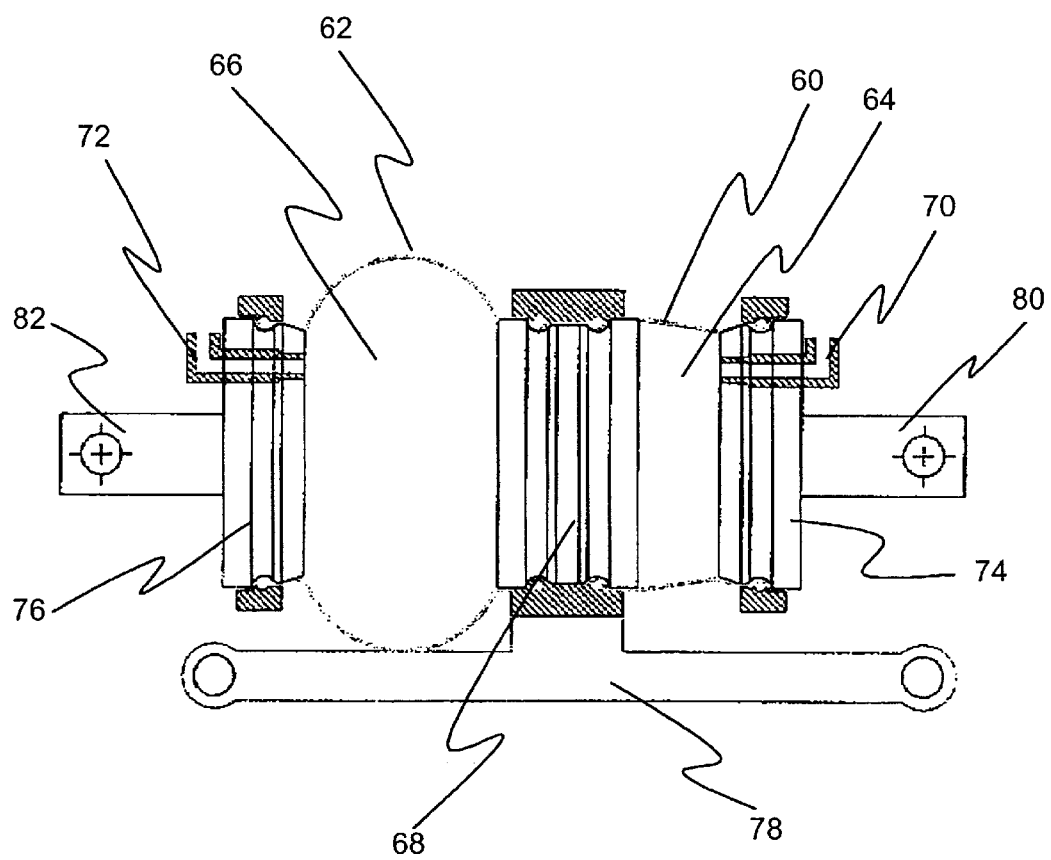
FIG. 6 is a cut-way side view of the hydraulic actuator of FIG. 5, shown here with the first side contracted and the second side expanded.

FIG. 6, illustrates the reverse operation of FIG. 5. That is, the fluid is pumped out of expandable fluid-containing cell 64 causing it to contract as flexible wall 60 is displaced, and end housing 74, and therefore connection-element 80, move toward the central base 68 and connection-element 78. Simultaneously, as the fluid is pumped into expandable fluid-containing cell 66 it expands as flexible wall 62 displaces, and end housing 76, and therefore connection-element 82, moves away from the central base 68 and connection-element 78. As the two expandable fluid-containing cells respectively expand and contract, the two end housings, and thereby their two connection-elements, move, in relation to the central base 68 and connection-element 78, in substantially the same direction while maintaining a substantially constant distance apart. This relative movement in relation to the central base may be utilized with, for example, but not limited to, a fixed central base and displaceable connection-elements 80 and 82, or fixed connection-elements 80 and 82 and a displaceable central base. The placement of the expandable fluid-containing cells need not be limited to opposite sides of the base, as shown here. Alternative embodiments may include, by non-limiting example, those with cell placement on sides that are perpendicular to each other, or placement of the cells on the same side of the base.

Figure 7:
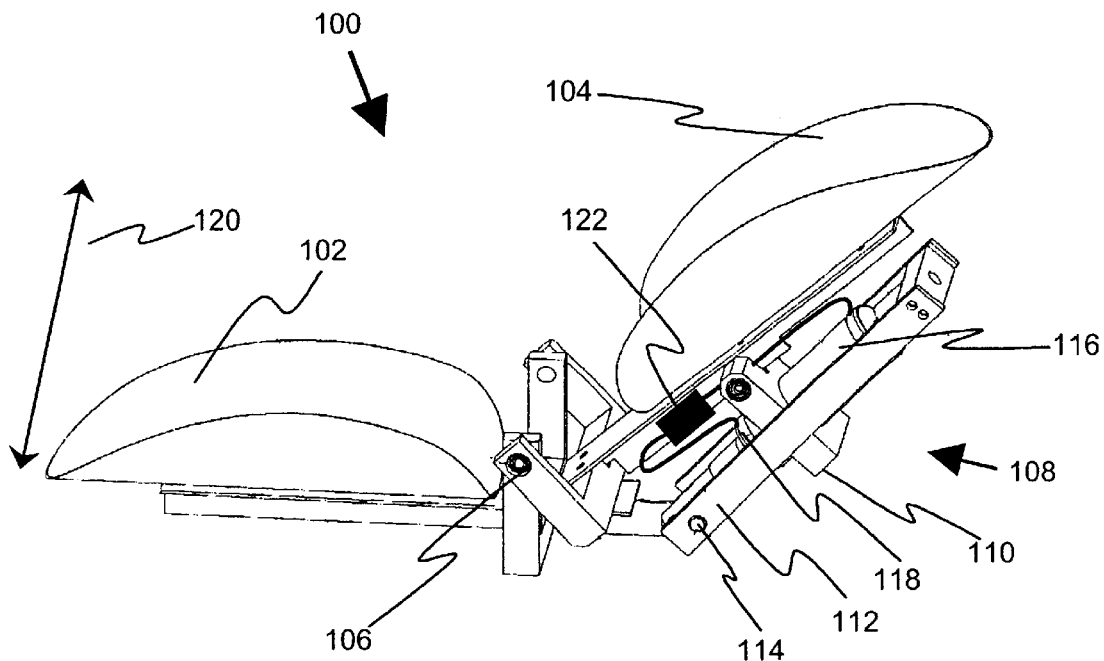
FIG. 7 is a perspective view of an orthetic device that is actuated by the preferred embodiment of FIG. 5.

A first non-limiting example on an application device that may be articulated by the hydraulic actuated artificial muscle of the present invention is that of the orthetic device shown in FIG. 7. Here, by non-limiting example, the device is configured with the hydraulic actuator of FIGS. 5 and 6. As illustrated, the orthetic device 100 includes a forearm attachment component 102 and an upper arm attachment component 104. These two components are hingedly attached by hinge pins 106. The device is articulated by a hydraulic actuator 108 as described in FIGS. 5 and 6. The central base 110 of the actuator is fixedly attached to the upper arm component. The displaceable end housings are attached to an articulation component 112 that is hingedly attached to the forearm attachment component at hinge pin 114. In operation, the pump 122 transfers fluid between expandable fluid-containing cells 116 and 118 causing the forearm attachment component to rotate about hinge pins 106 as illustrated by the arrow 120. The hydraulic actuator may be controlled, by non-limiting example, by a microprocessor that regulates operational parameters such as, but not limited to, direction, force, speed and amount of articulation. In the example shown, the microprocessor may be activated by a switch accessible to the user or an assistant.

Figure 8:
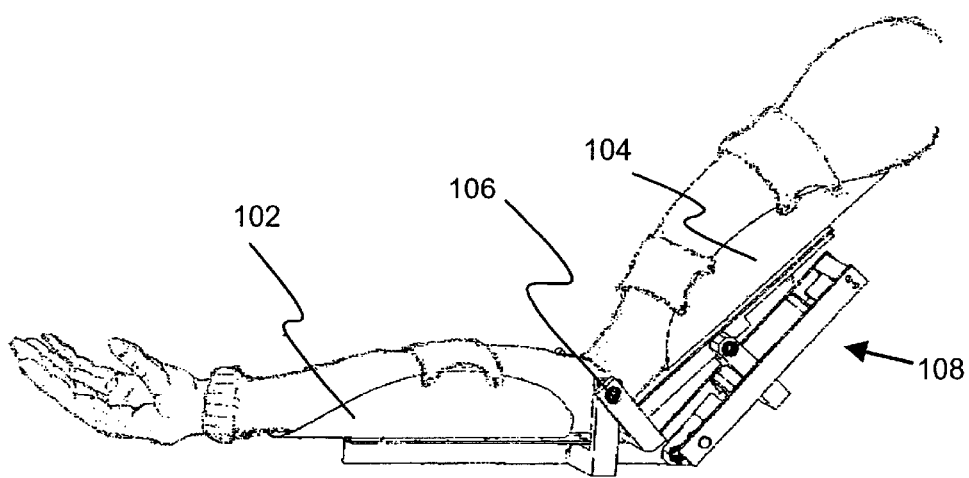
FIG. 8 is a perspective view of the orthetic device of FIG. 7 in place on a human arm.
Figure 9:
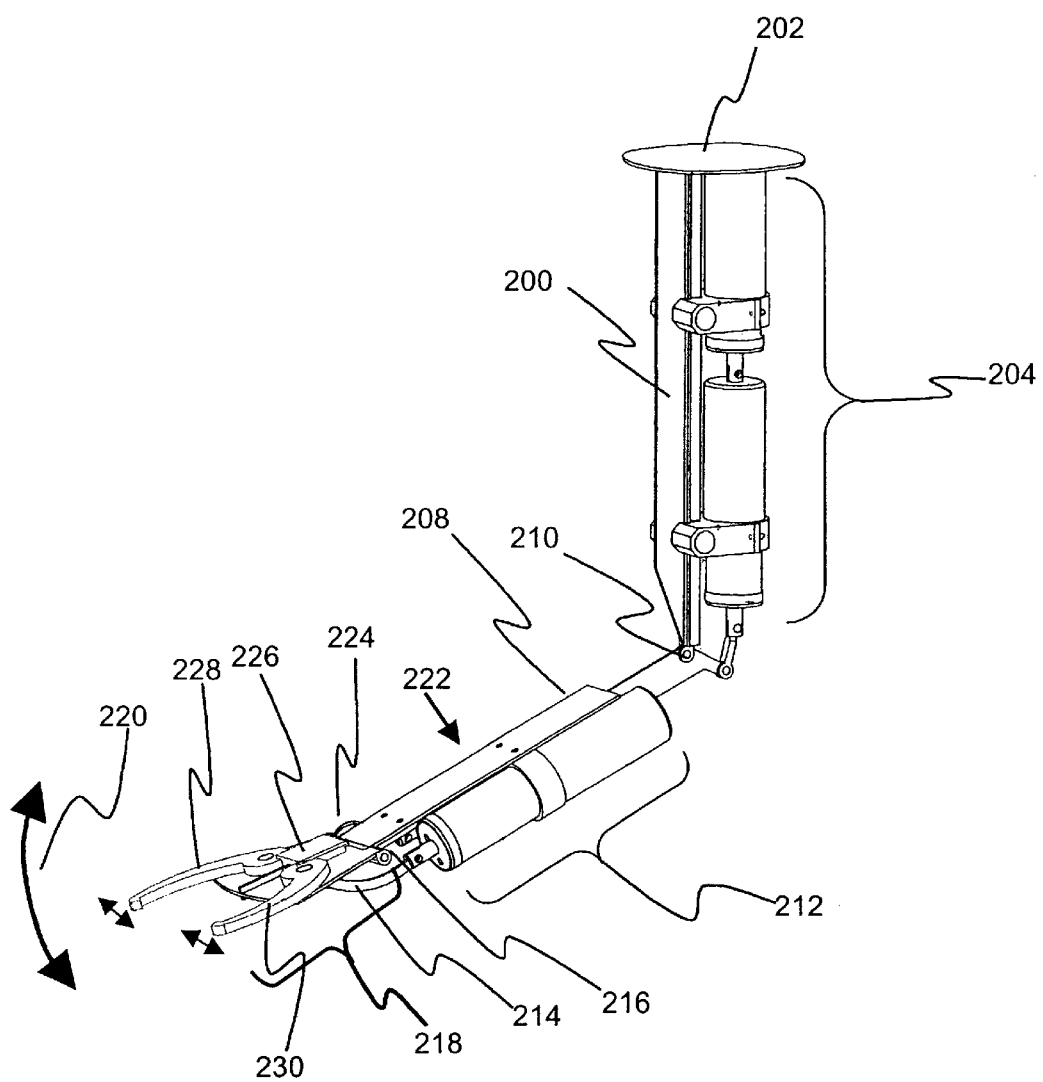
FIG. 9 is a perspective view of a prosthetic device that is articulated by multiple actuators of the preferred embodiment of FIG. 5.

FIG. 8 shows the orthetic device of FIG. 7 deployed on a human arm and is correspondingly numbered.

Another non-limiting example on an application device that may be articulated by the hydraulic actuated artificial muscle of the present invention is that of the prosthetic device shown in FIG. 8. This device is intended to replace a missing arm. The prosthesis is attached to the used by the attachment plate 202. Mounted on the upper-arm frame member 200 are a pair of artificial muscles 204 and 206 which articulate the lower-arm frame member 208 so as to rotate about axis 210. Artificial muscle 212 mounted on the lower-arm frame actuates the connector rod 214 so as to rotate the artificial hand 218 about the wrist hinge 216 as indicated by arrow 220. A fourth artificial muscle, indicated by arrow 222, is deployed adjacent to artificial muscle 212 so as to be hidden is this view. This fourth artificial muscle is used to actuate a cable 224 which in turn moves a linear gear element 226 so as to cause the fingers 228 and 230 of the artificial hand to open and close.

The size of the expandable fluid-containing cells may be varied to accommodate the needs of a particular application. It will be obvious to one skilled in the art, that there is a full range of applications to which this actuator is suited. A non-limiting list may include: Orthetic devices that can articulate any joint, either individually or in combinations; articulated prosthetic devices; and robotics. Activation can range from manually controlled "on-off" switches to fully programmed computerized routines.

It should be noted that while the non-limiting examples of preferred embodiments of the present invention described herein include two expandable fluid-containing cells, this is not intended as a limitation to the present invention. If the demands of a particular application may be met using more than two actively contributing expandable fluid-containing cells coupled with an appropriate pumping configuration creating one or more closed fluid systems, it is considered to be within the intent of the present invention.

It will be appreciated that the above descriptions are intended only to serve as examples, and that many other embodiments are possible within the spirit and the scope of the present invention.

What is claimed is:

1. A method for causing relative movement between at least two connecting elements, the at least two connecting elements being for attaching a hydraulic actuator to an application device, the method comprising:

transferring incompressible fluid between at least one first expandable fluid-containing cell and at least one second expandable fluid-containing cell such that said transferring of incompressible fluid out of one of said first expandable fluid-containing cell and said second expandable fluid-containing cell and into an other of said first expandable fluid-containing cell and said second expandable fluid-containing cell thereby causing substantially simultaneous contracting of said one and expanding of said other of said first expandable fluid-containing cell and said second expandable fluid-containing cell, said transferring being performed using a pump system in fluid communication with said first expandable fluid-containing cell and said second expandable fluid-containing cell thereby forming a closed fluid system;

wherein said at least one first expandable fluid-containing cell is at least partially defined by a first displaceable containment-wall, said first expandable fluid-containing cell being mechanically linked to at least a first of the connecting elements, said at least one second expandable fluid-containing cell is at least partially defined by a second displaceable containment-wall, said second expandable fluid-containing cell being mechanically linked to at least a second of the connecting elements, and at least one of said first displaceable containment-wall and second displaceable containment-wall is a flexible wall and said expanding of each of said expandable fluid-containing cells generates relative movement between at least two of the connecting elements.

2. The method of claim 1, wherein said transferring is performed between said at least one first expandable fluid-containing cell and said at least one second expandable fluid-containing cell configured such that one of said first displaceable containment-wall and second displaceable containment-wall defines at least portions of both said first expandable fluid-containing cell and said second expandable fluid-containing cell.

3. The method of claim 2, wherein said transferring is performed between said at least one first expandable fluid-containing cell and said at least one second expandable fluid-containing cell configured such that said first expandable fluid-containing cell substantially circumscribes said second expandable fluid-containing cell.

4. The method of claim 3, wherein said transferring is performed such that said expanding of said first expandable fluid-containing cell and said expanding of said second expandable fluid-containing cell are such that as fluid is pumped out of said first expandable fluid-containing cell and into said second expandable fluid-containing cell, said second expandable fluid-containing cell expands, thus causing the hydraulic actuator to expand longitudinally while contracting latitudinally thereby causing at least two of said connection elements to move substantially away from each other, conversely as fluid is pumped out of said second expandable fluid-containing cell and into said at least a first expandable fluid-containing cell, said first expandable fluid-containing cell expands, thus causing the hydraulic actuator to contract longitudinally while expanding latitudinally thereby causing at least two of the connection elements to move substantially toward each other.

5. The method of claim 3, wherein said transferring is performed between said at least one first expandable fluid-containing cell and said at least one second expandable fluid-containing cell configured such that both said first displaceable containment-wall and said second displaceable containment-wall are implemented as flexible walls.

6. The method of claim 3, wherein said transferring is performed between said at least one first expandable fluid-containing cell and said at least one second expandable fluid-containing cell configured such that said second displaceable containment-wall is implemented as a cylindrical wall of a piston element of a cylinder and piston assembly, said piston being displaceable within said cylinder.

7. The method of claim 1, wherein said transferring is performed between said at least one first expandable fluid-containing cell and said at least one second expandable fluid-containing cell configured such that said first expandable fluid-containing cell is deployed on a first side of a central base, said central base including at least a first of the connecting element, and second expandable fluid-containing cell is deployed on a second side of said central base, at least a second of the connecting elements is attached to said first expandable fluid-containing cell, at least a third of the connecting elements is attached to said at least one second expandable fluid-containing cell, said expanding of said first expandable fluid-containing cell and said expanding of said second expandable fluid-containing cell are such that as said fluid is pumped out of said first expandable fluid-containing cell and into said second expandable fluid-containing cell, said second expandable fluid-containing cell expands, thereby causing a first at least two of the connection elements to move substantially away from each other, conversely as fluid is pumped out of said second expandable fluid-containing cell and into said first expandable fluid-containing cell, said first expandable fluid-containing cell expands, thereby causing a second at least two of the connection elements to move substantially away from each other.

8. The method of claim 7, wherein said transferring is performed between said at least one first expandable fluid-containing cell and said at least one second expandable fluid-containing cell configured such that both said at least a first displaceable containment-wall and said at least a second displaceable containment-wall are implemented as said flexible walls.

9. The method of claim 7, wherein said transferring is performed between said at least one first expandable fluid-containing cell and said at least one second expandable fluid-containing cell configured such that said first side and said second side are substantially opposite sides of said central base.

10. The method of claim 1, further comprising said transferring being performed so as to articulate an orthetic device.

11. The method of claim 1, further comprising said transferring being performed so as to articulate a prosthetic device.

12. A hydraulic actuator comprising:
(a) at least two connecting elements for attaching the hydraulic actuator to an application device;
(b) at least one first expandable fluid-containing cell at least partially defined by a first displaceable containment-wall, said first expandable fluid-containing cell being mechanically linked to at least a first of said connecting elements;
(c) at least one second expandable fluid-containing cell at least partially defined by a second displaceable containment-wall, said second expandable fluid-containing cell being mechanically linked to at least a second of said connecting elements; and
(d) a pump system in fluid communication with said first expandable fluid-containing cell and said second expandable fluid-containing cell thereby forming a closed fluid system, said pump system configured to transfer incompressible fluid out of one of said first expandable fluid-containing cell and said second expandable fluid-containing cell and into an other of said first expandable fluid-containing cell and said second expandable fluid-containing cell, thereby causing substantially simultaneous contraction of said one and expansion of said other of said first expandable fluid-containing cell and said second expandable fluid-containing cell;

wherein at least one of said first displaceable containment-wall and second displaceable containment-wall is a flexible wall and said expansion of each of said expandable fluid-containing cells generates relative movement between at least two of said connecting elements.

13. The hydraulic actuator of claim 12, wherein one of said first displaceable containment-wall and second displaceable containment-wall defines at least portions of both said first expandable fluid-containing cell and said second expandable fluid-containing cell.

14. The hydraulic actuator of claim 13, wherein said first expandable fluid-containing cell substantially circumscribes said second expandable fluid-containing cell.

15. The hydraulic actuator of claim 14, wherein said expansion of said first expandable fluid-containing cell and said expansion of said second expandable fluid-containing cell are configured such that as fluid is pumped out of said first expandable fluid-containing cell and into said second expandable fluid-containing cell, said second expandable fluid-containing cell expands, thus causing the hydraulic actuator to expand longitudinally while contracting latitudinally thereby causing at least two of said connection elements to move substantially away from each other, conversely as fluid is pumped out of said second expandable fluid-containing cell and into said at least a first expandable fluid-containing cell, said first expandable fluid-containing cell expands, thus causing the hydraulic actuator to contract longitudinally while expanding latitudinally thereby causing at least two of said connection elements to move substantially toward each other.

16. The hydraulic actuator of claim 15, wherein both said first displaceable containment-wall and said second displaceable containment-wall are implemented as flexible walls.

17. The hydraulic actuator of claim 15, wherein said second displaceable containment-wall is implemented as a cylindrical wall of a piston element of a cylinder and piston assembly, said piston being displaceable within said cylinder.

18. The hydraulic actuator of claim 12, wherein said at least two connecting elements are implemented as at least three connecting elements, at least a portion of a first said connecting element being configured as a central base, at least a second said connecting element being attached to said first expandable fluid-containing cell deployed on a first side of said central base and at least a third said connecting elements being attached to said second expandable fluid-containing cell deployed on a second side of said central base, said expansion of said first expandable fluid-containing cell and said expansion of said second expandable fluid-containing cell are such that as fluid is pumped out of said first expandable fluid-containing cell and into said second expandable fluid-containing cell, said second expandable fluid-containing cell expands, thereby causing a first at least two of said connection elements to move substantially away from each other, conversely as fluid is pumped out of said second expandable fluid-containing cell and into said first expandable fluid-containing cell, said first expandable fluid-containing cell expands, thereby causing a second at least two of said connection elements to move substantially away from each other.

19. The hydraulic actuator of claim 18, wherein both said at least a first displaceable containment-wall and said at least a second displaceable containment-wall are implemented as said flexible walls.

20. The hydraulic actuator of claim 18, wherein said first side and said second side are substantially opposite sides of said central base.

21. The hydraulic actuator of claim 12, wherein said application device is an orthetic device.

22. The hydraulic actuator of claim 12, wherein said application device is a prosthetic device.

* * * * *